United States Patent
Jadhav

(10) Patent No.: US 11,793,935 B2
(45) Date of Patent: Oct. 24, 2023

(54) FLOATER BASED FLOW CONTROL DEVICE FOR GRAVITY IV SETS

(71) Applicant: CareFusion 303, Inc., San Diego, CA (US)

(72) Inventor: Amarsinh Deeliprao Jadhav, Bangalore (IN)

(73) Assignee: CareFusion 303, Inc., San Diego, CA (US)

(\*) Notice: Subject to any disclaimer, the term of this patent is extended or adjusted under 35 U.S.C. 154(b) by 529 days.

(21) Appl. No.: 16/936,334

(22) Filed: Jul. 22, 2020

(65) Prior Publication Data
US 2022/0023534 A1    Jan. 27, 2022

(51) Int. Cl.
*A61M 5/168*    (2006.01)
*A61M 5/14*    (2006.01)

(52) U.S. Cl.
CPC ...... *A61M 5/16813* (2013.01); *A61M 5/1411* (2013.01)

(58) Field of Classification Search
CPC ............ A61M 5/16813; A61M 5/1411; A61M 5/1407; A61M 5/16827; A61M 39/10; A61M 39/223; A61M 2039/2406; A61M 2039/2493; A61M 39/24; A61M 5/14; A61M 5/40; F16K 31/22
See application file for complete search history.

(56) References Cited

U.S. PATENT DOCUMENTS

| | | | |
|---|---|---|---|
| 3,586,038 A | 6/1971 | Jahrstorfer | |
| 2005/0194047 A1 | 9/2005 | Bausmith, III | |
| 2005/0273062 A1* | 12/2005 | Franksson | A61M 5/16881 604/254 |
| 2006/0264841 A1 | 11/2006 | Cote, Sr. et al. | |
| 2020/0025308 A1 | 1/2020 | Carmody et al. | |

FOREIGN PATENT DOCUMENTS

WO    WO-2017062110 A1    4/2017
WO    WO-2019136779 A1    7/2019

OTHER PUBLICATIONS

International Search Report and Written Opinion for Application No. PCT/US2021/042627, dated Oct. 28, 2021, 18 pages.

* cited by examiner

*Primary Examiner* — Amber R Stiles
*Assistant Examiner* — Nelson Louis Alvarado, Jr.
(74) *Attorney, Agent, or Firm* — Morgan, Lewis & Bockius LLP

(57) ABSTRACT

A flow control device includes an upper housing, a lower housing, a chamber interposed between and defined by the upper and lower housings, and a valve member. The upper housing includes a primary inlet having an internal surface defining a cavity and a secondary inlet. The lower housing defines an outlet of the flow control device. The chamber fluidly connects the primary and secondary inlets with the outlet. A valve member is reciprocally disposed at least partially in the cavity and partially in the chamber to (i) selectively permit fluid flow in the primary inlet in a first direction when a fluid level in the chamber is below a predetermined level, and (ii) prevent fluid backflow in a second direction opposite to the first direction when the fluid level in the chamber is above the predetermined level.

20 Claims, 8 Drawing Sheets

FLOATER BASED FLOW CONTROL DEVICE FOR GRAVITY IV SETS

TECHNICAL FIELD

The present disclosure generally relates to flow control devices, and more particularly to flow control devices having a valve member capable of preventing under-infusion in IV sets with a secondary line, as well as preventing backflow of drug from the secondary line into the primary line.

BACKGROUND

Infusion IV sets are generally used in infusion therapy in order to deliver medication from a pre-filled container, e.g., an IV bottle or bag containing the desired medication, to a patient. Generally, the IV tubing is connected to a catheter and inserted into the localized area to be treated. In some cases, there is a need to deliver multiple medications to the patient in potentially differing dosages, thereby causing the need for an IV extension set having multiple branches of tubings or fluid lines through which the multiple medications may be dispensed to the patient.

Patients are commonly injected with IV solutions that are initially provided in the IV bottle or bag and dripped into the vein of the patient through an IV line. A flow control device, for example, a check valve, is also commonly included in the IV line to permit fluid flow only in the direction of the patient. This ensures that the medication flows downstream toward the patient, not upstream toward the IV bottle or bag.

During infusion with IV sets, a secondary drug feed could potentially flow backwards into primary IV line leading to under infusion of the secondary drug. Though a check valve may be positioned in the primary line to prevent backflow, check valves may fail. A common reason for check valve failure is due to debris existing in infusates. Additionally, under-infusion frequently occurs due to air entering the secondary line thereby causing some of the secondary drug to remain in the secondary line (undelivered medication). Air entering the IV line may have undesirable effects such as causing air embolisms for the patient.

The description provided in the background section should not be assumed to be prior art merely because it is mentioned in or associated with the background section. The background section may include information that describes one or more aspects of the subject technology.

SUMMARY

In accordance with some embodiments of the present disclosure, a flow control device may include an upper housing including a primary inlet having an internal surface defining a cavity and a secondary inlet, a lower housing defining an outlet of the flow control device, and a chamber interposed between and defined by the upper and lower housings for fluidly connecting the primary and secondary inlets with the outlet. The valve member may be reciprocally disposed at least partially in the cavity and partially in the chamber to (i) selectively permit fluid flow in the primary inlet in a first direction when a fluid level in the chamber is below a predetermined level, and (ii) prevent fluid backflow in a second direction opposite to the first direction when the fluid level in the chamber is above the predetermined level.

In accordance with some embodiments, an intravenous (IV) set may include a primary IV line and a secondary IV line, and a flow control device. The flow control device may include an upper housing, a lower housing coupled to the upper housing, and a chamber defined between the upper and lower housings. The upper housing may include a primary inlet fluidly communicating the primary IV line with the chamber, and a secondary inlet fluidly communicating the secondary IV line with the chamber. The flow control device may further include a valve member having a base disposed in the chamber and a plurality of legs extending longitudinally from the base into the primary inlet, the floating valve member being displaceable in a proximal direction by a buoyant force exerted on the base when a level of fluid in the chamber exceeds a predetermined level.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
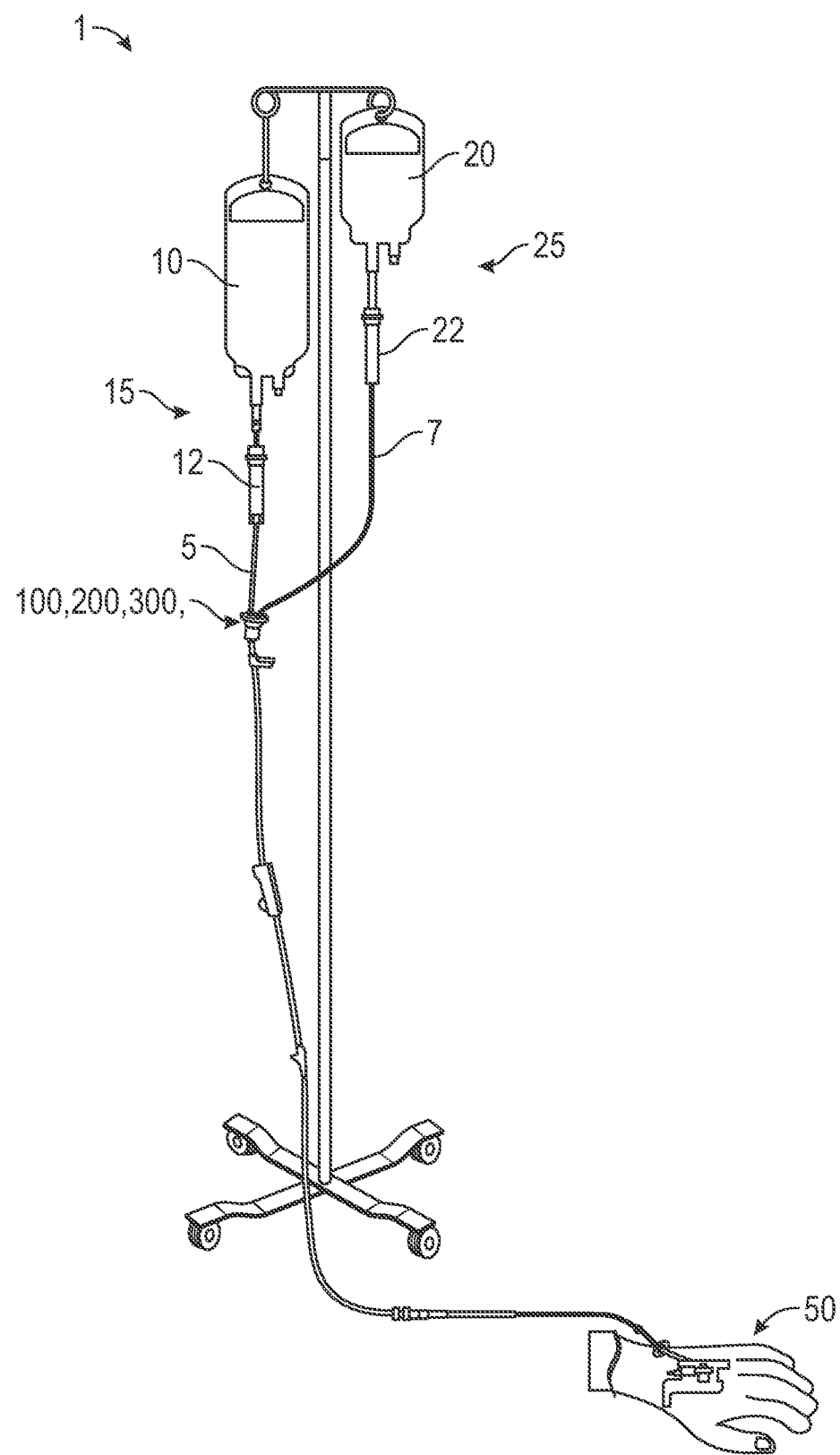
FIG. 1 illustrates a multiple line IV extension set that includes a flow control device, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present description relates in general to flow control devices, and more particularly to flow control devices having a valve member capable of preventing under infusion in IV sets with a secondary line, as well as preventing backflow of drug from the secondary line into the primary line.

IV sets with a secondary line tend to experience under-infusion of the secondary drug due to failure of the check valve in the primary line. The most frequent causes of failure of the check valve are due to debris accumulated at the time of spiking and seeping of drug in the secondary line into the primary line at low pressures. A common cause of under-infusion is dilution of drug at the time of back priming of the secondary IV and also at the time of equal head in the primary and secondary lines. Other causes include dead volume in the secondary line, as well as time taken to infuse the drug. The flow control devices of the various embodiments described herein overcome the above issues commonly associated with IV sets having primary and secondary lines.

In accordance with various embodiments of the present disclosure, a flow control device may include an upper housing having a primary inlet and a secondary inlet, a lower housing coupled to the upper housing, a chamber defined between the upper and lower housings, and a floating valve member disposed at least partially in the chamber and partially in the primary inlet. In some embodiments, the upper housing may have an internal surface with a circumferential lip at a distal end thereof. The circumferential lip may be oriented projecting radially inwards towards a central longitudinal axis of the primary inlet.

In some embodiments, the valve member may have a base and a plurality of legs extending longitudinally from the base into the primary inlet. The legs may be spaced apart from each other with adjacent pairs of the legs each defining a flow portion or slot through which fluid entering the primary inlet flows into the chamber. In some embodiments, each of the legs may terminate in a flange at a proximal end of the valve member. In other embodiments, the valve member may be structured as a body with a central aperture and a plurality of axially extending slots through which fluid flowing into the primary inlet may enter the chamber.

In operation, when the fluid level in the chamber is below a predetermined level, and when the valve member is subject to a net upstream force (i.e., a force applied by a fluid flowing from the primary inlet towards the chamber that exceeds that of any buoyant force applied by fluid in the chamber), the valve member may be translated distally (downstream) to a position where each flange is seated on the circumferential lip. Accordingly, the valve member may be placed in an open state whereby fluid from the primary IV line may enter the chamber via the primary inlet.

In accordance with some embodiments, the valve member may include a sealing member coupled to at least a portion of an upper surface of the base.

In operation, when the fluid level in the chamber is above a predetermined level and when the valve member is subject to a net downstream force (i.e., a buoyant force applied by a fluid in the chamber that exceeds any upstream force applied by a fluid flowing from the primary inlet towards the chamber), the valve member may be translated proximally (upstream) to a position where the sealing member contacts and seals against the internal surface of the upper housing. Accordingly, fluid flow from the chamber into the primary inlet is blocked, thereby preventing fluid backflow into the primary inlet. As such, under-infusion of the secondary drug, which commonly occurs as a result of the secondary drug flowing back into the primary inlet from the chamber, is prevented. Preventing backflow of the fluid is advantageous in that it restricts undesirable particulate matter, for example, contained in the secondary drug from flowing back through the valve member and preventing the patient from receiving the proper drug dosage concentration or from timely delivery of the drug.

FIG. 1 illustrates a multiple line IV extension set 1 that includes a flow control device 100, 200, 300, in accordance with some embodiments of the present disclosure. IV set 1 includes a primary fluid system 15 and a secondary fluid system 25. An IV pump (not shown) receives fluid from primary fluid system 15 and secondary fluid system 25 via a primary IV line 5 and may control and dispense the fluids therefrom to a patient 50.

In some embodiments, primary fluid system 15 may include a primary fluid source such as a primary fluid bag 10 which may include or contain saline solution or other medicinal fluid or drug to be administered to the patient 50. As illustrated, primary IV line 5 carries primary fluid from a drip chamber 12 to flow control device 100, 200, 300. As shall be described further with respect to the following figures, flow control device 100, 200, 300 may be disposed in primary IV line 5 and allow fluid flow from primary fluid bag 10 to the IV pump (not illustrated) while preventing reverse flow (backflow) of fluid from secondary fluid system 25 toward primary fluid bag 10. In accordance with some embodiments, secondary fluid system 25 includes secondary fluid source such as a secondary fluid bag 8, which may contain drugs or other secondary fluid to be supplied to the patient 50 for treatment. As depicted, the IV set 1 may further include a secondary IV line 7 which carries flow from drip chamber 22 to the flow control device 100, 200, 300.

Figure 2A:
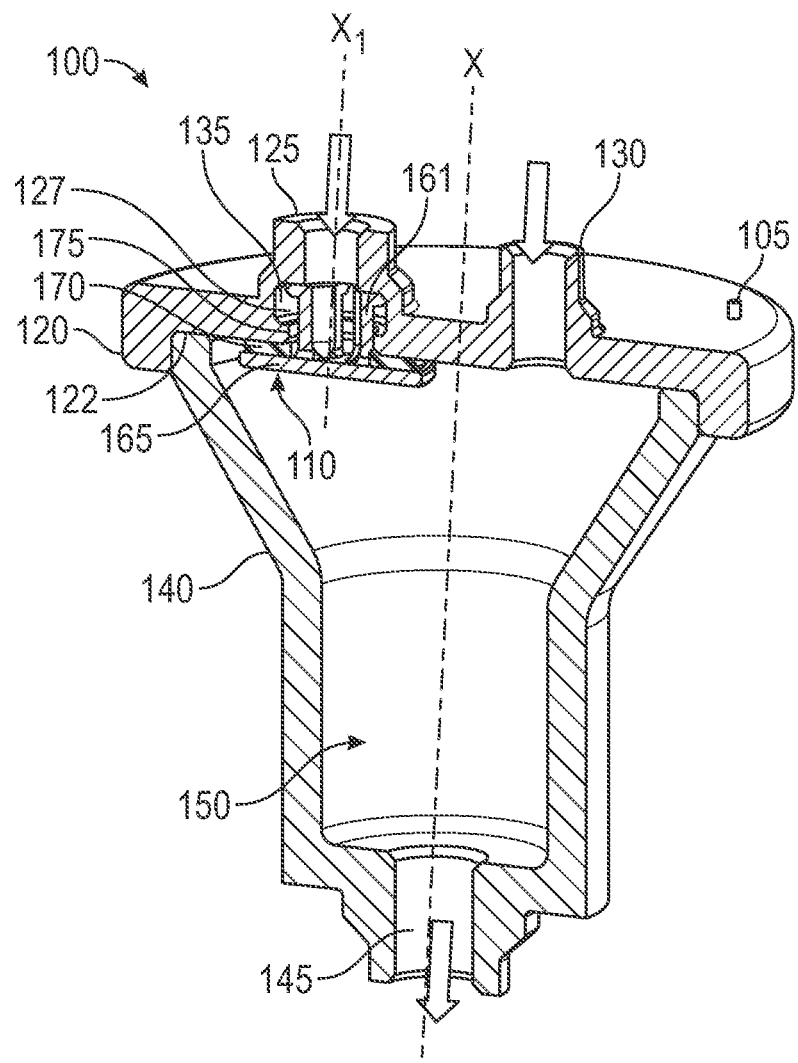
FIG. 2A illustrates a cross-sectional view of a flow control device, in accordance with some embodiments of the present disclosure.
Figure 2B:
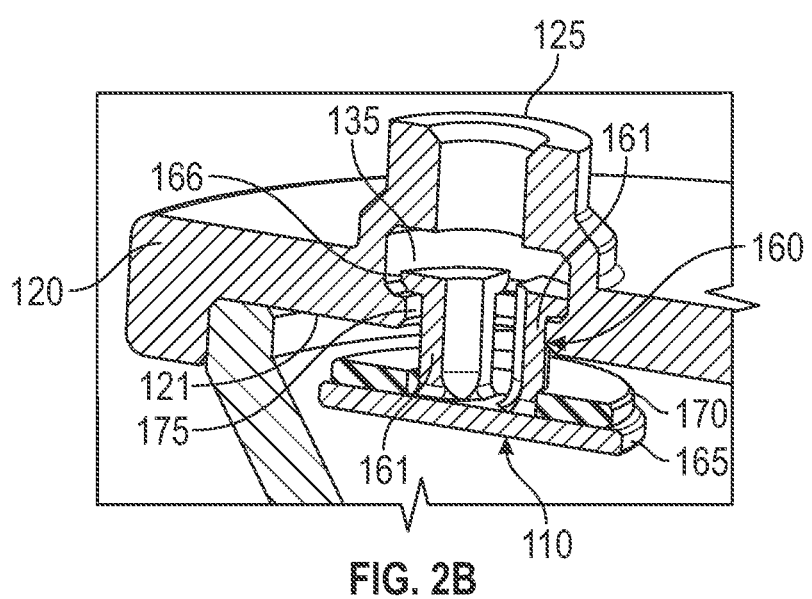
FIG. 2B illustrates an enlarged partial cross-sectional view of the flow control device and valve member of FIG. 2A, in accordance with some embodiments of the present disclosure.

FIG. 2A illustrates a cross-sectional view of a flow control device 100, in accordance with some embodiments of the present disclosure. FIG. 2B illustrates an enlarged partial cross-sectional view of the flow control device 100 and valve member of FIG. 2A, in accordance with some embodiments of the present disclosure. As depicted, the flow control device 100 may include an upper housing 120, a lower housing 140 coupled to the upper housing 120, a chamber 150 defined between the upper housing 120 and the lower housing 140, and a floating valve member 110 disposed at least partially in the chamber. The upper housing may also include a secondary inlet 130 for fluidly communicating the secondary IV line 7 with the chamber 150. In some embodiments, an air vent 105 is positioned on the upper housing for removing air during priming. Referring to FIG. 2A, the flow control device is displayed in cross-sectional view to more clearly illustrate some of the features of the valve member 110. As depicted, the flow control device 100 may be in the form of an axially extending body defining a central longitudinal axis X. The body may be generally cylindrical (or tubular) or may have any other shape with a hollow interior capable of defining a chamber.

Figure 2C:
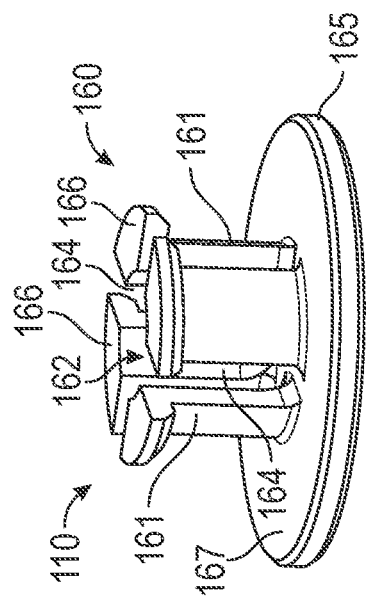
FIG. 2C illustrates a perspective view of an upper housing of the flow control device of FIG. 2A in accordance with some embodiments.
Figure 2D:
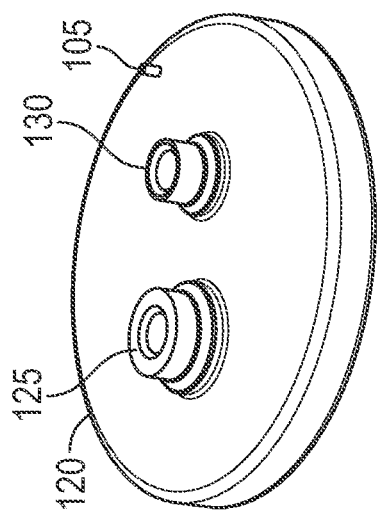
FIG. 2D illustrates a cross-sectional view of the upper housing of the flow control device of FIG. 2A in accordance with some embodiments.

FIG. 2C illustrates a perspective view of an upper housing of the flow control device of FIG. 2A in accordance with some embodiments. FIG. 2D illustrates a cross-sectional view of the upper housing of the flow control device of FIG. 2A in accordance with some embodiments. Referring to FIGS. 2C and 2D, the upper housing 120 may include a primary inlet 125 for fluidly communicating the primary IV line 5 with the chamber 150. As depicted, the primary inlet 125 may have an internal surface 127, which defines a cavity 135 in which at least a portion of the valve member 110 is disposed. The cavity 135 may form a part of the primary inlet 125, or may be otherwise fluidly communicated with the primary inlet 125. Accordingly, fluid flowing from the primary inlet 125 to the chamber 150 may flow via the cavity 135. In some embodiments, the internal surface 127 defining the cavity may have a circumferential lip 175 at a distal end thereof. As depicted, the circumferential lip 175 may be oriented projecting radially inwards towards a central longitudinal axis Xi (illustrated in FIG. 2A) of the primary inlet 125.

Referring back to FIG. 2A, in some embodiments of the present disclosure the lower housing 140 may be coupled distally to the upper housing 120, and may further define an outlet 145 through which medication or drugs from the primary and secondary inlets may be delivered to the patient 50. As illustrated, a radial extent of the lower housing 140 at a proximal end thereof (the end directly coupled to the upper housing 120) may be greater than the radial extent at a distal end. However, the various embodiments of the present disclosure are not specifically limited to the aforementioned configuration and a shape and configuration of the lower housing 140 may vary for the intended purposes while still embodying the working principles described herein. The lower housing 140 and the upper housing 120 may axially contact each other to co-operatively form the chamber 150 of the flow control device 100. In the depicted embodiments, the floating valve member 110 may be mounted partially in the cavity 135 and partially in the chamber 150. The floating valve member 110 may selectively permit fluid flow from the primary IV line 5, through the primary inlet 125, and into the chamber 150 when a fluid level in the chamber 150 falls below a predetermined level Further, the valve member 110 may operate to prevent fluid backflow into the primary inlet 125 from the secondary inlet 130 and the chamber 150 when the fluid level in the chamber 150 is above the predetermined level and exerts a buoyant force on the valve member 110.

Figure 3:
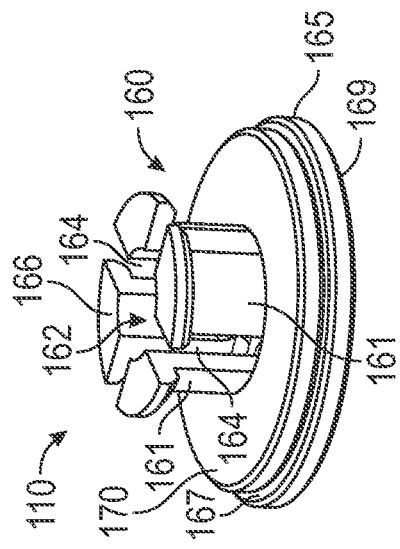
FIG. 3 illustrates a perspective view of a valve member of a flow control device, in accordance with some embodiments of the present disclosure.

FIG. 3 illustrates a perspective view of a valve member 110 of a flow control device, in accordance with some embodiments of the present disclosure. According to various aspects of the present disclosure, the valve member 110 may include a base 165 and a main body 160 extending proximally from the base 165. In some embodiments, the base 165 may be in the form of a disc or any other circular or semi-circular plate having an upper surface 167 and a lower surface 169. The size or surface area of the base 165 may be selected specifically to allow for maximum exposure to the fluid in the chamber 150 so as to overcome fluid force of the fluid entering the primary inlet 125 from the primary IV tubing 5. For example, the greater the size of the base 165, the greater the surface area acted upon by the fluid in the chamber. Accordingly, the valve member 110 may be designed so as open and close the primary inlet based on a specific threshold force.

As depicted, the main body 160 may have a plurality of legs 161 extending longitudinally from the base 165 into the cavity 135 of the primary inlet 125. The legs 161 may each extend longitudinally from an upper surface 167 of the base 165. In some embodiments, the legs 161 may be oriented substantially perpendicularly with respect to the upper surface 167 of the base 165. In particular, the legs 161 may extend and protrude substantially perpendicularly at a height above the upper surface 167 of the base 165. In some embodiments, the legs 161 may be spaced apart from each other at regular intervals. For example, the valve member 110 may have two or more legs 161 equally spaced apart from each other. In other embodiments, the legs 161 may be spaced apart from each other at irregular intervals. As depicted, adjacent pairs of the legs 161 each define a flow portion or slot 164 through which fluid entering the cavity 135 from the primary inlet 125 flows into the chamber 150. As illustrated, each of the legs 161 may terminate in a flange 166 at a proximal end of the valve member 110.

In some embodiments, the legs 161 may have a polygonal shape, for example a rectangular, square or any other suitable polygonal shape terminating in the flange 166. In other embodiments, the legs 161 may have a curved shape, for example a circular, an oval or oblong shape terminating in the flange 166. However, the various embodiments of the present disclosure are not limited the aforementioned configurations, and the shape and spacing of the legs 161 from each other may be varied as desired.

In other embodiments, the main body 160 may be structured with a central aperture 162 and a plurality of axially extending slots 164 through which fluid flowing into the primary inlet 125 and into the cavity 135 may enter the chamber 150.

In operation, when subject to a net upstream force (i.e., a force applied by a fluid flowing from the primary inlet 125 towards the chamber 150 that exceeds that of any buoyant force applied by fluid in the chamber 150), the valve member 110 may be translated distally (downstream) to a position where flange 166 is seated on the circumferential lip as illustrated in FIG. 2B. Accordingly, the valve member 110 may be placed in an open state whereby fluid from the primary IV line 5 may enter the chamber 150 via the primary inlet 125.

Figure 4:
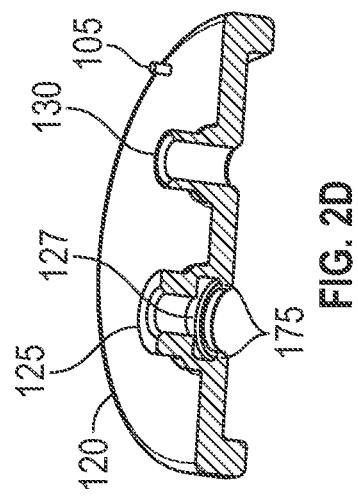
FIG. 4 illustrates a perspective view of a valve member and sealing member of a flow control device, in accordance with some embodiments of the present disclosure.

FIG. 4 illustrates a perspective view of a valve member 110 and sealing member 170 of a flow control device 100, in accordance with some embodiments of the present disclosure. As depicted, the valve member 110 may include a sealing member 170 coupled to at least a portion of an upper surface 167 of the base 165. The sealing member 170 may be configured to contact and seal against an internal surface 122 of the upper housing 120.

In operation, when subject to a net downstream force (i.e., a buoyant force applied by a fluid in the chamber 150 that exceeds any upstream force applied by a fluid flowing from the primary inlet 125 towards the chamber 150), the valve member 110 may be translated proximally (upstream) to a position where sealing member 170 contacts and seals against the internal surface 122 of the upper housing 120, as illustrated in FIG. 2A. Accordingly, fluid flow from the chamber 150 into the primary inlet 125 is blocked, thereby preventing fluid backflow into the primary inlet 125. Similarly, under-infusion of the secondary drug which commonly occurs as a result of the secondary drug flowing back into the primary inlet 125 from the chamber 150 may be prevented. Preventing backflow of the fluid is advantageous in that it restricts undesirable particulate matter, for example, contained in a drug dispensed from the secondary IV line 7 from flowing back through the valve member 110, thereby preventing the patient 50 from receiving the proper drug dosage concentration or from timely delivery of the drug.

Figure 5:
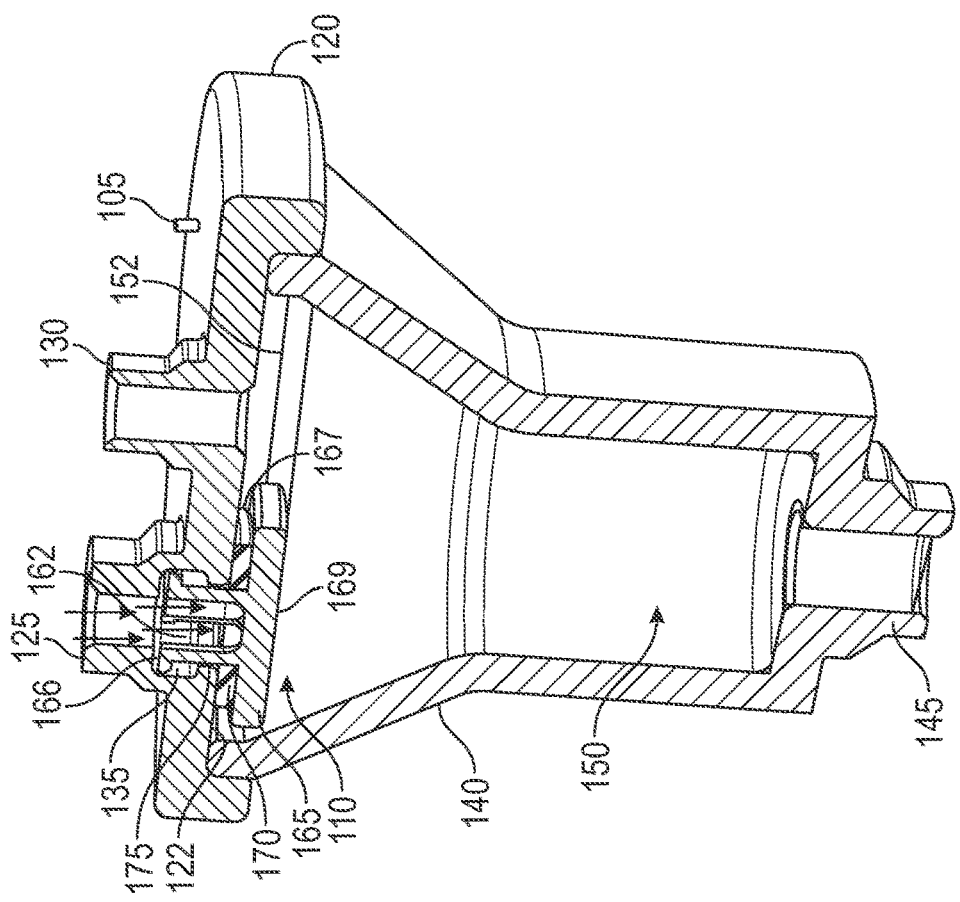
FIG. 5 is a cross-sectional view of a flow control device in an open state when subjected to an upstream force, where the drug level in the chamber is below a predetermined level, in accordance with some embodiments of the present disclosure.

FIG. 5 is a cross-sectional view of a flow control device in an open state when subjected to an upstream force, where the drug level in the chamber is below a predetermined level and the valve member permits fluid flow from the primary inlet into the chamber, in accordance with some embodiments of the present disclosure. As depicted, during operation, fluid may enter the flow control device 100 via the primary inlet 125, and flow through the cavity 135 and into the chamber 150 via the flow portions or slots 164 between adjacent pairs of the legs 161. Where the fluid level in the chamber 150 is below a predetermined level, the upstream force (i.e., force applied by fluid flowing from the primary IV line 5 into the primary inlet 125) applied to the valve member 110 causes the valve member 110 to be displaced or otherwise move distally and be seated on the circumferential lip 175. Thus, the primary inlet 125 is placed in an open state where the primary inlet 125, the cavity 135, and the chamber 150 are fluidly communicated. In the open state, fluid from the primary IV line may flow into the chamber 150 via the cavity 135 and the flow portions or slots 164 between adjacent pairs of the legs 161. As the fluid from the primary IV line continues to enter the chamber 150, the fluid level 152 rises until such a point that the fluid in the chamber contacts the lower surface 169 of the base 165 of valve member 110. Once the fluid level 152 rises above a predetermined level, the fluid in the chamber exerts a buoyant force on the base 165, which is greater in magnitude than the upstream force applied by the fluid flowing from the primary IV line 5 into the primary inlet 125. Accordingly, the valve member 110 is then translated proximally to a position where the sealing member 170 contacts and seals against the internal surface 122 of the upper housing 120, thereby placing the primary inlet 125 in the closed state, as illustrated in FIG. 6.

Figure 6:
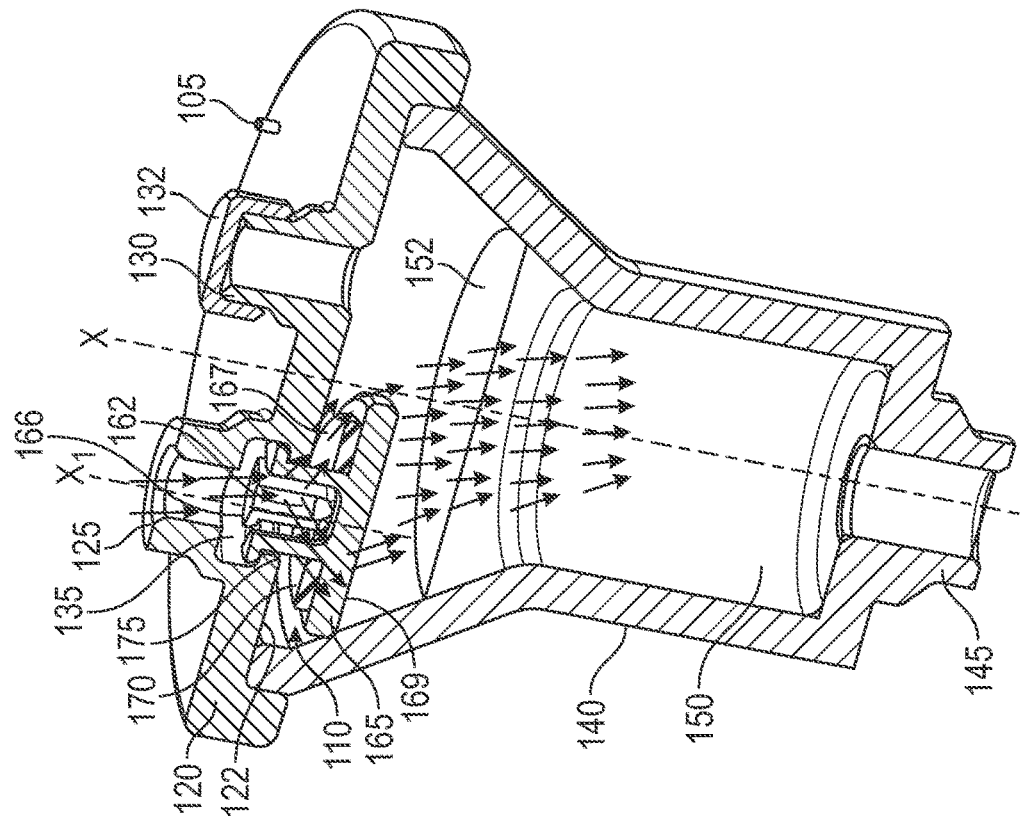
FIG. 6 is a cross-sectional view of the flow control device of FIG. 5 in a closed state, where the drug level is above a predetermined amount and applies a buoyant force to the valve member, in accordance with some embodiments of the present disclosure.

FIG. 6 is a cross-sectional view of the flow control device of FIG. 5 in a closed state, where the drug level is above a predetermined amount and applies a buoyant force to the valve member to block fluid flow from the primary inlet into the chamber and prevent backflow into the primary inlet, in accordance with some embodiments of the present disclosure. As depicted, during operation, when the buoyant force that exceeds the force of the fluid flowing in the primary IV line 5 is applied to the base 165 of valve member 110, the sealing member 170 contacts and seals against the internal surface 122 of the upper housing 120. The primary inlet 125 is thereby placed in the closed state, and dispensing of the drug or other fluid from the primary inlet 125 into the chamber ceases. At this time the secondary drug or other fluid in the secondary IV line 7 may be dispensed into the chamber 150 via the secondary inlet 130.

Advantageously, since flow from the primary inlet 125 into the chamber 150 is blocked at this time, the secondary drug may be dispensed and flow into the chamber 150 without the possibility of flowing backwards into the primary inlet 125 and potentially diluting the drug in the primary IV line 5. Accordingly, under-infusion of the secondary drug or fluid caused by the secondary drug or fluid flowing backwards into the primary IV line 5 may be prevented.

Preventing backflow of the fluid is further advantageous in that it restricts undesirable particulate matter, for example, contained in the drug or fluid dispensed from the secondary IV line 7 from flowing back through the valve member 110, thereby preventing the patient from receiving the proper drug dosage concentration or from timely delivery of the drug(s) to the patient 50.

Figure 7:
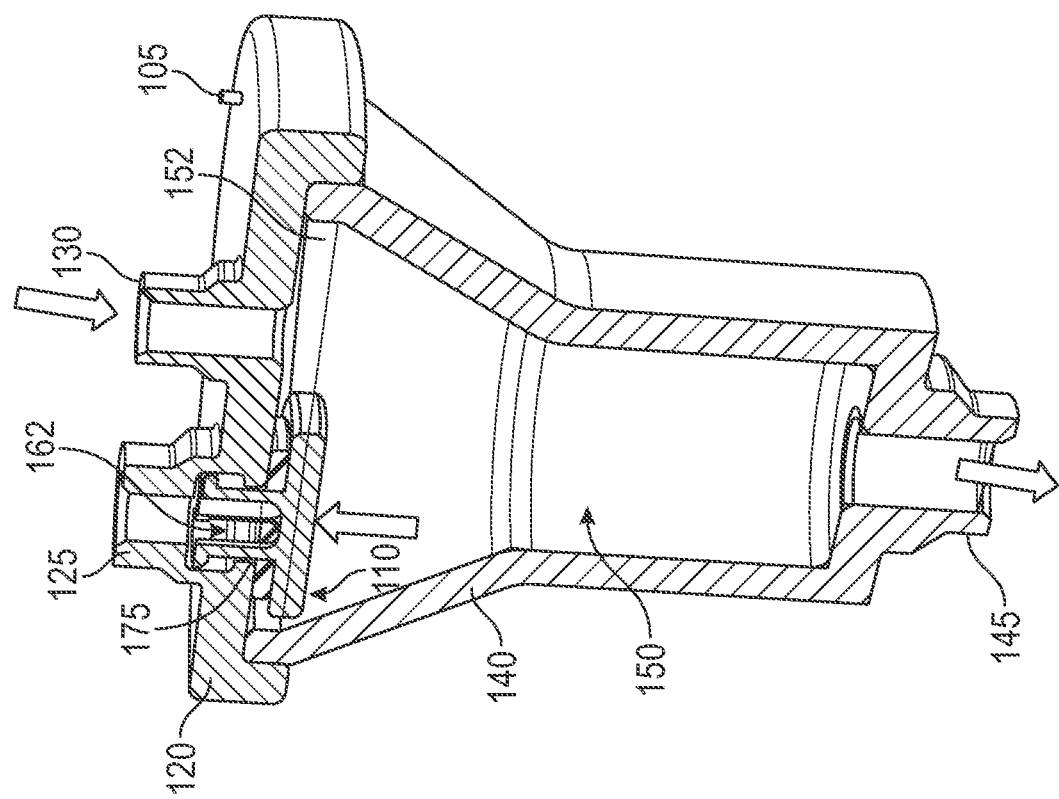
FIG. 7 is a cross-sectional view of the flow control device of FIG. 5 in a closed state, where fluid flows from the secondary inlet into the chamber in accordance with some embodiments of the present disclosure.

FIG. 7 is a cross-sectional view of the flow control device of FIG. 5 in a closed state, where fluid flows from the secondary inlet into the chamber in accordance with some embodiments of the present disclosure. As depicted, during operation, the secondary drug may be dispensed into the chamber 150 via the secondary inlet 130 until such time that the secondary drug dispensing is complete. During this time, fluid in the chamber 150 may also be dispensed to the patient 50 via the outlet 145. As fluid continues to be dispensed to the patient 50 via the outlet 145, the fluid level 152 in the chamber 150 continues to decrease until the fluid level is below the predetermined level as illustrated in FIG. 8.

Figure 8:
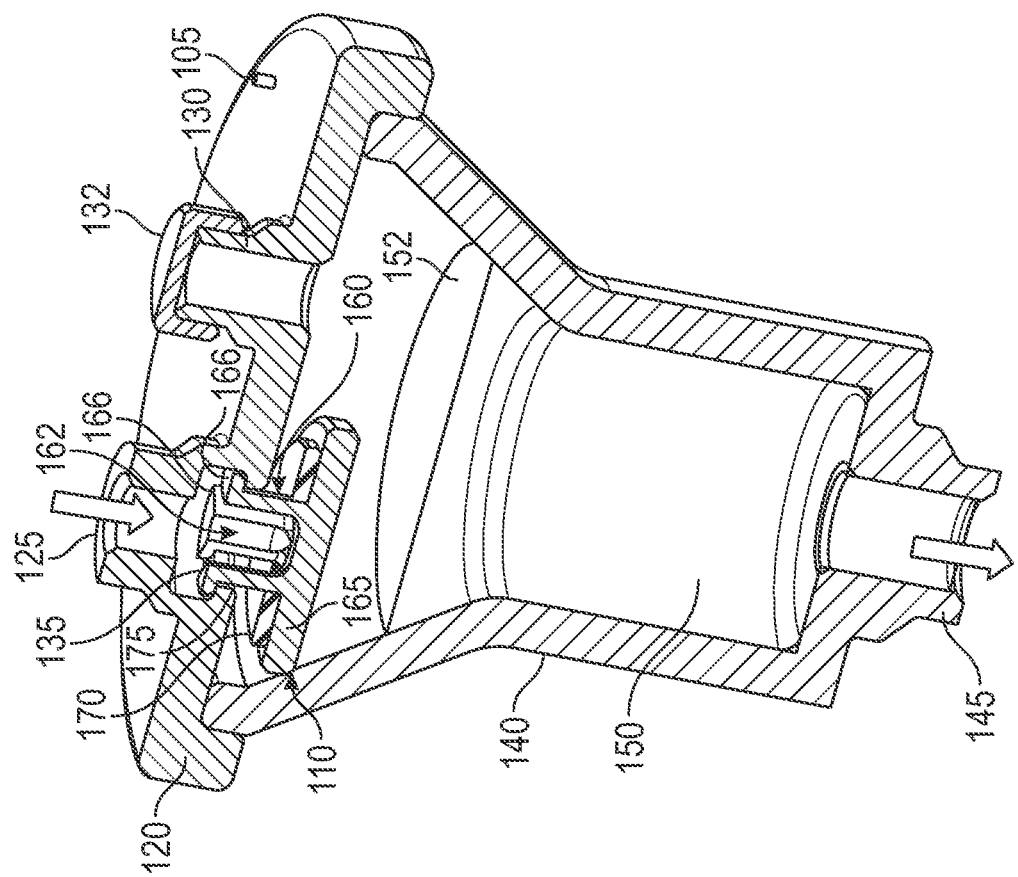
FIG. 8 is a cross-sectional view of the flow control device of FIG. 5 in an open state, where fluid flow from the secondary inlet into the chamber is complete, and the drug level in the chamber has fallen below a predetermined level, in accordance with some embodiments of the present disclosure.

FIG. 8 is a cross-sectional view of the flow control device of FIG. 5 in an open state, where fluid flow from the secondary inlet into the chamber is complete, and the drug level in the chamber has fallen below a predetermined level and the valve member is displaced by fluid force to resume flow from the primary inlet into the chamber, in accordance with some embodiments of the present disclosure. As the drug in the chamber 150 continues to be dispensed to the patient via the outlet 145, the level of fluid in the chamber 150 falls below the predetermined level and the magnitude of the buoyant force diminishes. As a result, the valve member 110 is displaced distally (towards the chamber 150) and the fluid flow from the primary IV line into the chamber 150 via the primary inlet 125 resumes. As depicted, the upstream force applied to the valve member 110 causes the valve member 110 to seat on the circumferential lip 175. Accordingly, the primary inlet 125 is placed in an open state where the primary inlet 125, the cavity 135, and the chamber 150 are fluidly communicated. In the open state, fluid from the primary IV line 5 may flow into the chamber 150 via the cavity 135 and the flow portions or slots 164 between adjacent pairs of the legs 161.

Table 1, illustrated below provides exemplary calculations for buoyant force and upstream force applied to the valve member 110 based on exemplary dimensions of the valve member 110. Although the specific dimensions of the valve member 110 are used in the calculations below, the various embodiments of the present disclosure are not limited to these specific dimensions. The dimensions of the valve member 110 may be varied based on the desired purpose, and the buoyant force and upstream force applied may also vary proportionally based on the dimensions of the valve member 110. According to various embodiments of the present disclosure, the buoyant force is calculated using the following equation:

$$F_B = \rho_f V_f g,$$

where $F_B$ is the buoyant force, $\rho_f$ is the density of the displaced fluid, $V_f$ is the volume of the displaced fluid, and g is the acceleration due to gravity, 9.8 m/s².

TABLE 1

| Parameter | Value | Unit |
| --- | --- | --- |
| Volume of valve member base | 226.58 | mm³ |
|  | 0.000 | m³ |
| Buoyant force | $F_B = \rho_f V_f g$ |  |
| g | 9.81 | N/Kg |
| Density of drug | 997.00 | kg/m3 |
| Buoyant force | 2.22 | N |
| Weight of the body | 0.25 | gm |
|  | 0.0025 | N |
| Downward force due to primary line | 1.96 | N |
| Total downward force on the plate | 1.96 | N |
| Buoyant force | 2.21612 | N |

Accordingly, the various embodiments of the present disclosure are advantageous in providing a flow control device capable of preventing under-infusion of the secondary drug by blocking the secondary drug from flowing backwards into the primary IV line, as discussed previously. The flow control device of the various embodiments described herein is further advantageous as it minimizes the number of separate components of an IV set by replacing a check valve and a y-connector with the single flow control device. As a result, cost of the IV set may be reduced. Additionally, the various embodiments of the present disclosure are advantageous in reducing workflow steps for the clinician/nurses since no manual operation is necessary for flow regulation as the flow pressure of the secondary drug or fluid is used to regulate flow of the primary drug or fluid.

Advantageously, since flow from the primary inlet 125 into the chamber 150 is blocked at this time, the secondary drug may be dispensed and flow into the chamber 150 without the possibility of flowing backwards into the primary inlet 125 and potentially diluting the drug in the primary IV line 5. Accordingly, under-infusion of the secondary drug or fluid caused by the secondary drug or fluid flowing backwards into the primary IV line 5 is prevented.

Preventing backflow of the fluid is further advantageous in that it restricts undesirable particulate matter, for example, contained in the drug or fluid dispensed from the secondary IV line 7 from flowing back through the valve member 110, thereby preventing the patient from receiving the proper drug dosage concentration or from timely delivery of the drug(s) to the patient 50.

Figure 9:
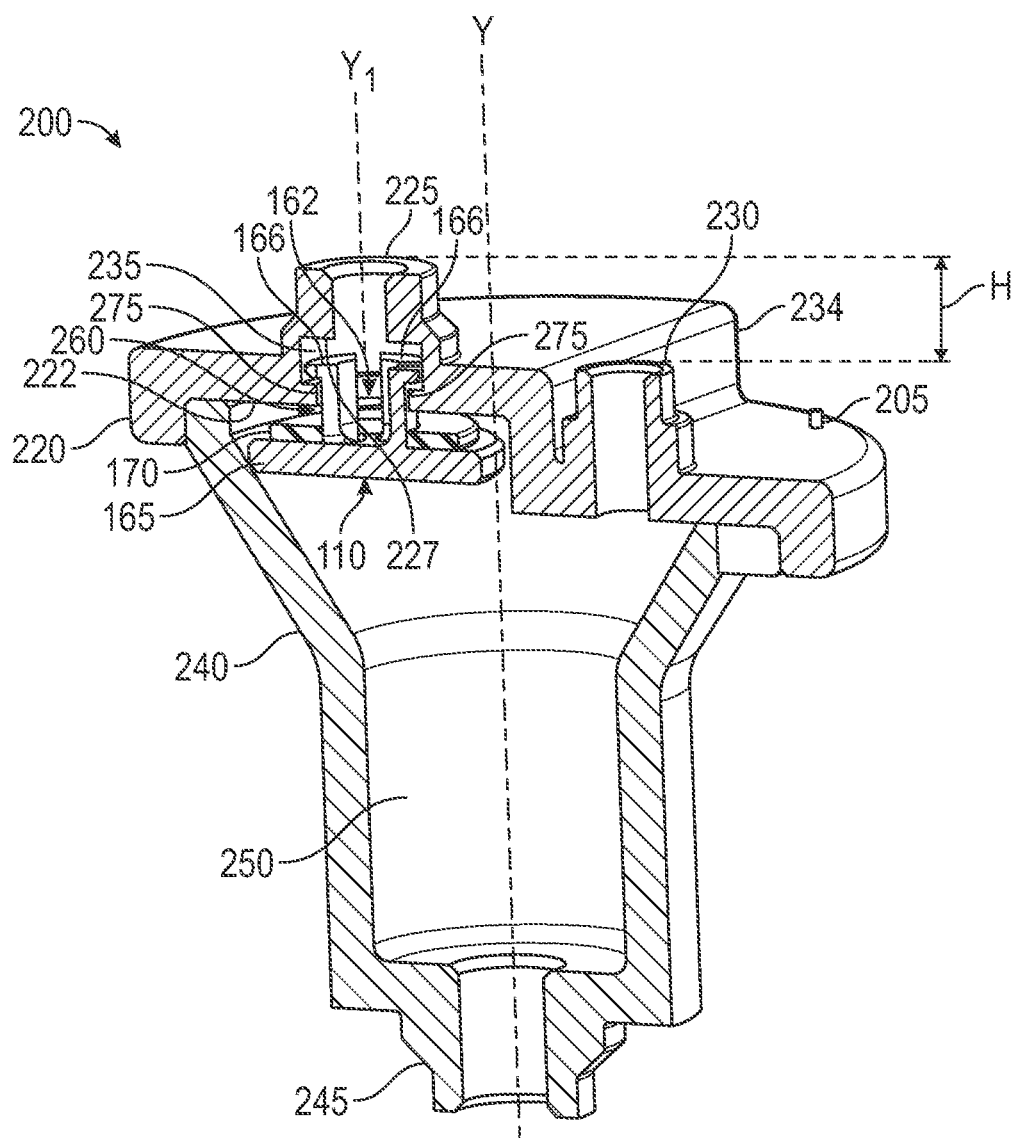
FIG. 9 illustrates a cross-sectional view of a flow control device having a valve member, in accordance with some embodiments of the present disclosure.

FIG. 9 illustrates a cross-sectional view of a flow control device 200 having a valve member 110, in accordance with some embodiments of the present disclosure. Referring to FIG. 9, similar to the embodiments of FIG. 2A, a flow control device 200 may include an upper housing 220, a lower housing 240 coupled to the upper housing 220, a chamber 250 defined between the upper housing 220 and the lower housing 240, and the floating valve member 110 disposed at least partially in the chamber 250. As depicted, the upper housing 220 may include a primary inlet 225 for fluidly communicating the primary IV line 5 with the chamber 250, and a secondary inlet 230 for fluidly communicating the secondary IV line 7 with the chamber 250. As depicted, the flow control device 100 may be in the form of an axially extending body defining a central longitudinal axis Y. The body may be generally cylindrical (or tubular) or may have other shapes with a hollow interior capable of defining a chamber.

Similar to the embodiments of FIG. 2A, the primary inlet 225 may have an internal surface 227, which defines a cavity 235 in which at least a portion of the valve member 110 is disposed. The cavity 235 may form a part of the primary inlet 225, or may be otherwise fluidly communicated with the primary inlet 225. Therefore, fluid flowing from the primary inlet 225 to the chamber 250 may flow via the cavity 235. In some embodiments, the internal surface 227 defining the cavity may have a circumferential lip 275 at a distal end thereof. As depicted, the circumferential lip 275 may be oriented projecting radially inwards towards a central longitudinal axis Yi of the primary inlet 225.

In accordance with various embodiments of the present disclosure, the lower housing 240 may be coupled distally to the upper housing 220, and may further define an outlet 245 through which medication or drugs from the primary and secondary inlets 225 and 230 may be delivered to the patient 50. Similar to the embodiments of FIG. 2A, a radial extent of the lower housing 240 at a proximal end thereof (the end directly coupled to the upper housing 220) may be greater than the radial extent at a distal end thereof. However, the various embodiments of the present disclosure are not specifically limited to the aforementioned configuration and a shape and configuration of the lower housing may vary for the intended purposes while still embodying the working principles described herein. The lower housing 240 and the upper housing 220 may axially contact each other to co-operatively form the chamber 250 of the flow control device 200. In the depicted embodiments, the floating valve member 110 may be mounted partially in the cavity 235 and partially in the chamber 250 to selectively permit fluid flow from the primary IV line 5, through the primary inlet 125, and into the chamber 250 when a fluid level in the chamber 250 falls below a predetermined level. Furthermore, the valve member 110 may operate to prevent fluid backflow from the secondary inlet 230 and the chamber 250 when the fluid level in the chamber 250 is above the predetermined level and exerts a buoyant force on the valve member 110.

In accordance with various embodiments of the present disclosure, and in contrast to the flow control device 100, the secondary inlet 230 of the flow control device 200 may be positioned at a lower axial position (distally) than the primary inlet 225 with the valve member 110 mounted therein. For example, secondary inlet 230 may be positioned a predetermined height H below the primary inlet 225 with mounted valve member 110. The aforementioned configuration ensures that the valve member 110 remains above the level of the secondary line to allow the valve member 210 to function as intended.

Figure 10:
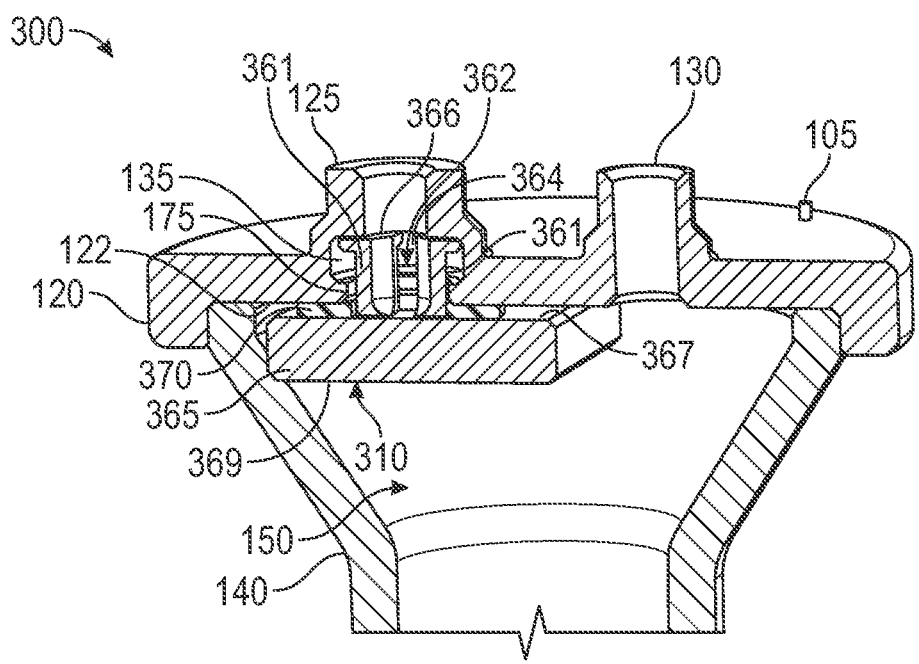
FIG. 10 illustrates a cross-sectional view of a flow control device having a valve member, in accordance with some embodiments of the present disclosure.

FIG. 10 illustrates a cross-sectional view of a flow control device 300 having a valve member 310, in accordance with some embodiments of the present disclosure. Referring to FIG. 10, similar to the embodiments of FIG. 2A, the flow control device 300 may include an upper housing 120, a lower housing 140 coupled to the upper housing 120, and a chamber 150 defined between the upper housing 120 and the lower housing 140. As depicted, the upper housing 120 may include a primary inlet 125 for fluidly communicating the primary IV line 5 with the chamber 150, and a secondary inlet 130 for fluidly communicating the secondary IV line 7 with the chamber 150. Since the upper and lower housings 120 and 140, and the chamber 150 as well as their connection and fluid communication with respect to each other are identical as described above with respect to flow control device 100 of FIG. 2A, a further detailed description thereof shall be omitted with respect to the flow control device 300. According to various embodiments, the control device 300 may further include a valve member 310 disposed at least partially in the chamber 150.

Figure 11:
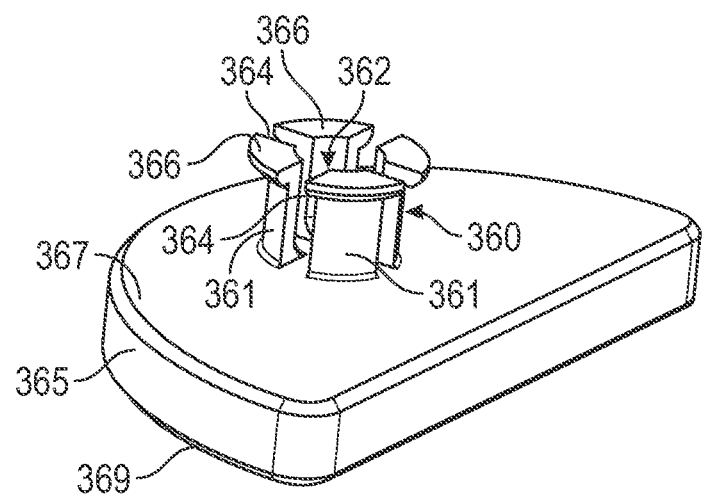
FIG. 11 illustrates a perspective view of the valve member of FIG. 10, in accordance with some embodiments of the present disclosure.

FIG. 11 illustrates a perspective view of the valve member of FIG. 10, in accordance with some embodiments of the present disclosure. As depicted, the valve member 310 may include a base 365 and a main body 360 extending proximally from the base 365. In some embodiments, the base 365 may be in the form of a disc or any other circular or semi-circular plate having an upper surface 367 and a lower surface 369. The size or surface area of the base 365 may be selected specifically to allow for maximum exposure to the fluid in the chamber 150 so as to overcome fluid force of the fluid entering the primary inlet 125 from the primary IV tubing 5. For example, the greater the size of the base 365, the greater the surface area acted upon by the fluid in the chamber 150. Accordingly, the valve member 310 may be designed so as open and close the primary inlet 125 based on a specific threshold force. In particular, the base 365 differs in structure to the base 165 of the various embodiment described in FIGS. 3 and 4 in that the base 365 may have a greater surface area than that of the base 165. For example, as illustrated, the base 365 may be in the shape of a semi-circular plate having a greater radius than the radius of the circular plate-shaped base 165. The aforementioned configuration of the base 365 may be further advantageous over that of the base 165 in that a greater fluid force from the primary IV line 5 will be required to displace the valve member 310 and open the primary inlet 125 when the level of fluid in the chamber 150 is above the predetermined level. This is the case because the greater surface area of the base 365 is subject to a larger buoyant force from the fluid in the chamber (see Table 2 below). Accordingly, the valve member 310 is less likely to leak or otherwise open when unintended as a result of excessive fluid pressure in the primary IV line 5.

Similar to the embodiments described above with respect to the valve member 110, the main body 360 of the valve member 310 may have a plurality of legs 361 extending longitudinally from the base 365 into the cavity 135 of the primary inlet 125. The legs 361 may each extend longitudinally from an upper surface 367 of the base 365. In some embodiments, the legs 361 may be oriented substantially perpendicularly with respect to the upper surface 367 of the base 365. In particular, the legs 361 may extend and protrude substantially perpendicularly at a predetermined height above the upper surface 367 of the base 365. In some embodiments, the legs 361 may be spaced apart from each other at regular intervals. For example, the valve member 310 may have two or more legs 361 equally spaced apart from each other. In other embodiments, the legs 361 may be spaced apart from each other at irregular intervals. As depicted, adjacent pairs of the legs 361 each define a flow portion or slot 364 through which fluid entering the cavity 135 from the primary inlet 125 flows into the chamber 150. As illustrated, each of the legs 361 may terminate in a flange 366 at a proximal end of the valve member 310.

In some embodiments, the legs 361 may have a polygonal shape, for example a rectangular, square or any other suitable polygonal shape terminating in the flange 366. In other embodiments, the legs 361 may have a curved shape, for example a circular, an oval or oblong shape terminating in the flange 366. However, the various embodiments of the present disclosure are not limited the aforementioned configurations, and the shape and spacing of the legs 361 from each other may be varied as desired.

In other embodiments, the main body 360 may be structured with a central aperture 362 and a plurality of axially extending slots 364 through which fluid flowing into the primary inlet 125 and into the cavity 135 may enter the chamber 150.

Since the operation and function of the flow control device 300 and valve member 310 is similar to that of the flow control device 100 and valve member 110, and a detailed description of how the flow control device 100 and valve member 110 function was provided above with respect to FIGS. 2A and 5-8, a detailed description thereof shall be omitted with respect to the flow control device 300 and valve member 310.

Table 2, illustrated below provides exemplary calculations for buoyant force and upstream force applied to the valve member 310 based on exemplary dimensions of the valve member 310. Although the specific dimensions of the valve member 310 are used in the calculations below, the various embodiments of the present disclosure are not limited to these specific dimensions. The dimensions of the valve member 310 may be varied based on the desired purpose, and the buoyant force and upstream force applied may also vary proportionally based on the dimensions of the valve member 310. According to various embodiments of the present disclosure, the buoyant force is calculated using the following equation:

$$F_B = \rho_f V_f g,$$

where $F_B$ is the buoyant force, $\rho_f$ is the density of the displaced fluid, $V_f$ is the volume of the displaced fluid, and g is the acceleration due to gravity, 9.8 m/s$^2$.

TABLE 2

| Parameter | Value | Unit |
| --- | --- | --- |
| Volume of valve member base | 243 | mm$^3$ |
|  | 0.000 | m$^3$ |
| Buoyant force | $F_B = \rho_f V_f g$ |  |
| g | 9.81 | N/Kg |
| Density of drug | 997.00 | kg/m3 |
| Buoyant force | 2.37667851 | N |
| Weight of the body | 0.22 | gm |
|  | 0.002156 | N |
| Downward force due to primary line | 1.96 | N |
| Total downward force on the plate | 1.962156 | N |
| Buoyant force | 2.37667851 | N |

Figure 12:
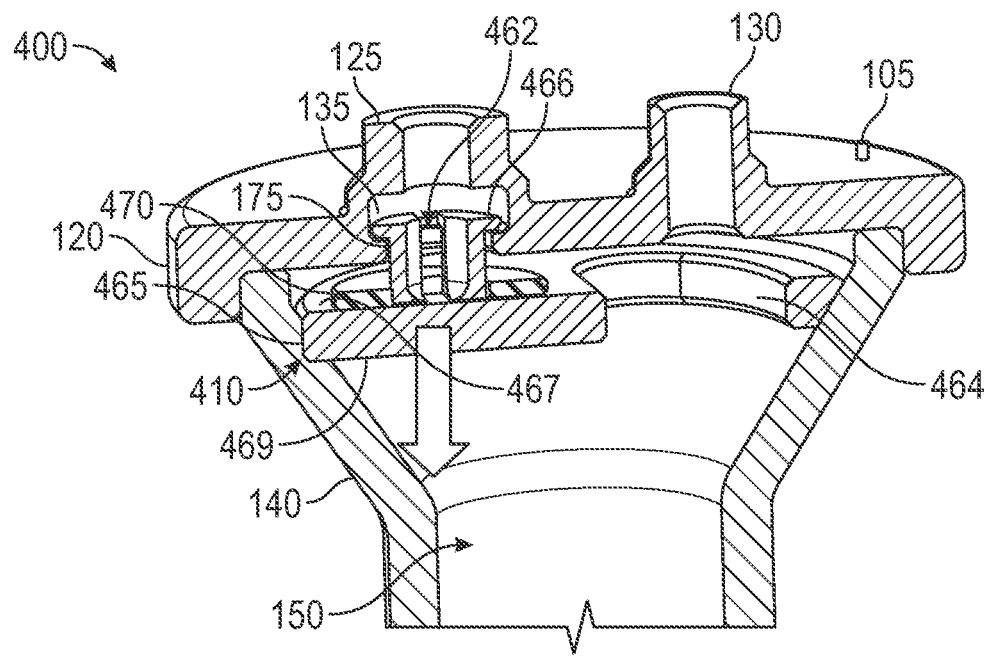
FIG. 12 illustrates a cross-sectional view of a flow control device having a valve member, in accordance with some embodiments of the present disclosure.

FIG. 12 illustrates a cross-sectional view of a flow control device 400 having a valve member 410, in accordance with some embodiments of the present disclosure. Referring to FIG. 12, similar to the embodiments of FIG. 2A, the flow control device 400 may include an upper housing 120, a lower housing 140 coupled to the upper housing 120, and a chamber 150 defined between the upper housing 120 and the lower housing 140. As depicted, the upper housing 120 may include a primary inlet 125 for fluidly communicating the primary IV line 5 with the chamber 150, and a secondary inlet 130 for fluidly communicating the secondary IV line 7 with the chamber 150. Since the upper and lower housings 120 and 140, and the chamber 150 as well as their connection and fluid communication with respect to each other are identical as described above with respect to flow control device 100 of FIG. 2A, a further detailed description thereof shall be omitted with respect to the flow control device 400. According to various embodiments, the control device 400 may further include a valve member 410 disposed at least partially in the chamber 150.

Figure 13:
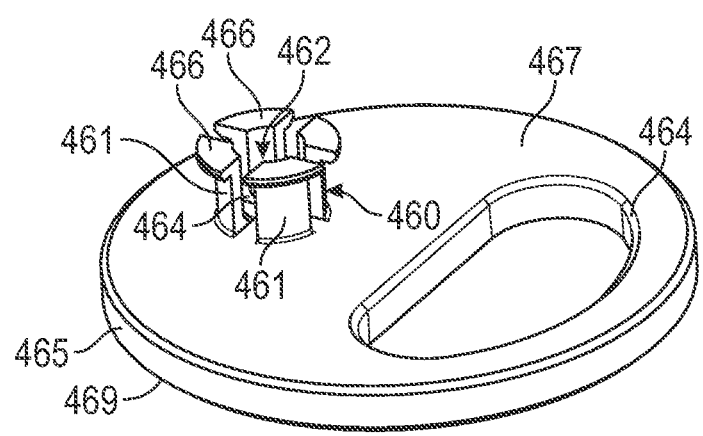
FIG. 13 illustrates a perspective view of the valve member of FIG. 12, in accordance with some embodiments of the present disclosure.

FIG. 13 illustrates a perspective view of the valve member 410 of FIG. 12, in accordance with some embodiments of the present disclosure. As depicted, the valve member 410 may include a base 465 and a main body 460 extending proximally from the base 465. In some embodiments, the base 465 may be in the form of a disc or any other circular or semi-circular plate having an upper surface 467 and a lower surface 469. The size or surface area of the base 465 may be selected specifically to allow for maximum exposure to the fluid in the chamber 150 so as to overcome fluid force of the fluid entering the primary inlet 125 from the primary IV tubing 5. For example, the greater the size of the base 465, the greater the surface area acted upon by the fluid in the chamber 150. Accordingly, the valve member 410 may be designed so as open and close the primary inlet 125 based on a specific threshold force. In particular, the base 465 differs in structure to the base 165 of the various embodiment described in FIGS. 3 and 4 in that the base 465 may have a greater surface area than that of the base 165. For example, as illustrated, the base 465 may be in the shape of a circular plate having a greater diameter than the diameter of the circular plate-shaped base 165 and spanning an area below both the primary and secondary inlets 125 and 130. As depicted, the base 465 may have an aperture 462 positioned at a location corresponding to an opening at a distal end of the secondary inlet 130 to prevent the base 465 from occluding fluid flow from the secondary inlet 7 into the chamber 150. The aforementioned configuration of the base 465 may be further advantageous over that of the base 165 in that a greater fluid force from the primary IV line 5 will be required to displace the valve member 410 (without obstructing flow through the secondary inlet 130) and open the primary inlet 125 when the level of fluid in the chamber 150 is above the predetermined level. This is the case because the greater surface area of the base 465 is subject to a larger buoyant force from the fluid in the chamber 150 (see Table 3 below). Accordingly, the valve member 410 is less likely to leak or otherwise open when not intended to as a result of excessive fluid pressure in the primary IV line 5.

Similar to the embodiments described above with respect to the valve member 110, the main body 460 of the valve member 410 may have a plurality of legs 461 extending longitudinally from the base 465 into the cavity 135 of the primary inlet 125. The legs 461 may each extend longitudinally from an upper surface 467 of the base 465. In some embodiments, the legs 461 may be oriented substantially perpendicularly with respect to the upper surface 467 of the base 465. In particular, the legs 461 may extend and protrude substantially perpendicularly at a predetermined height above the upper surface 467 of the base 465. In some embodiments, the legs 461 may be spaced apart from each other at regular intervals. For example, the valve member 410 may have two or more legs 461 equally spaced apart from each other. In other embodiments, the legs 461 may be spaced apart from each other at irregular intervals. As depicted, adjacent pairs of the legs 461 each define a flow portion or slot 464 through which fluid entering the cavity 135 from the primary inlet 125 flows into the chamber 150.

As illustrated, each of the legs 461 may terminate in a flange 466 at a proximal end of the valve member 410.

In some embodiments, the legs 461 may have a polygonal shape, for example a rectangular, square or any other suitable polygonal shape terminating in the flange 466. In other embodiments, the legs 461 may have a curved shape, for example a circular, an oval or oblong shape terminating in the flange 466. However, the various embodiments of the present disclosure are not limited the aforementioned configurations, and the shape and spacing of the legs 461 from each other may be varied as desired.

In other embodiments, the main body 460 may be structured with a central aperture 462 and a plurality of axially extending slots 464 through which fluid flowing into the primary inlet 125 and into the cavity 135 may enter the chamber 150.

Since the operation and function of the flow control device 400 and valve member 410 is similar to that of the flow control device 100 and valve member 110, and a detailed description of how the flow control device 100 and valve member 110 function was provided above with respect to FIGS. 2A and 5-8, a detailed description thereof shall be omitted with respect to the flow control device 400 and valve member 410.

Table 3, illustrated below provides exemplary calculations for buoyant force and upstream force applied to the valve member 410 based on exemplary dimensions of the valve member 410. Although the specific dimensions of the valve member 410 are used in the calculations below, the various embodiments of the present disclosure are not limited to these specific dimensions. The dimensions of the valve member 410 may be varied based on the desired purpose, and the buoyant force and upstream force applied may also vary proportionally based on the dimensions of the valve member 410. According to various embodiments of the present disclosure, the buoyant force is calculated using the following equation:

$$F_B = \rho_f V_f g,$$

where $F_B$ is the buoyant force, $\rho_f$ is the density of the displaced fluid, $V_f$ is the volume of the displaced fluid, and g is the acceleration due to gravity, 9.8 m/s$^2$.

TABLE 3

| Parameter | Value | Unit |
|---|---|---|
| Volume of valve member base | 245 | mm$^3$ |
|  | 0.000 | m$^3$ |
| Buoyant force | $F_B = \rho_f V_f g$ |  |
| g | 9.81 | N/Kg |
| Density of drug | 997.00 | kg/m3 |
| Buoyant force | 2.39623965 | N |
| Weight of the body | 0.22 | gm |
|  | 0.002156 | N |
| Downward force due to primary line | 1.96 | N |
| Total downward force on the plate | 1.962156 | N |
| Buoyant force | 2.39623965 | N |

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A flow control device, comprising:
    an upper housing including:
        a primary inlet having an internal surface defining a cavity; and
        a secondary inlet;
    a lower housing defining an outlet of the flow control device;
    a chamber interposed between and defined by the upper and lower housings for fluidly connecting the primary and secondary inlets with the outlet; and
    a valve member reciprocally disposed at least partially in the cavity and partially in the chamber to (i) selectively permit fluid flow in the primary inlet in a first direction when a fluid level in the chamber is below a predetermined level, and (ii) prevent fluid backflow in a second direction opposite to the first direction when the fluid level in the chamber is above the predetermined level, the valve member having a base and a main body, the main body comprising a plurality of legs extending longitudinally from the base into the cavity of the primary inlet and a flange at a proximal end of the main body.

2. The flow control device of claim 1, wherein the main body further comprises a central aperture and a plurality of axially extending slots through which fluid flowing into the primary inlet and the cavity enters the chamber.

3. The flow control device of claim 1, wherein:
the internal surface defining the cavity comprises a circumferential lip at a distal end thereof, the circumferential lip projecting radially inwards towards a central longitudinal axis of the primary inlet; and
the main body flange is configured to be seated on the circumferential lip when the valve member is subjected to a net axial force in the first direction.

4. The flow control device of claim 1, wherein the plurality of legs are radially spaced apart about a central longitudinal axis of the main body, and each spacing between adjacent legs defines a flow portion through which fluid entering the primary inlet and into the cavity enters the chamber.

5. The flow control device of claim 1, wherein:
each of the legs comprises a portion of the main body flange and the internal surface defining the cavity comprises a circumferential lip at a distal end thereof, the circumferential lip projecting radially inwards towards a central longitudinal axis of the primary inlet; and
each main body flange portion is configured to be seated on the circumferential lip when the valve member is subjected to a net axial force in the first direction.

6. The flow control device of claim 1, wherein the base comprises a substantially circular plate sharing a common central axis with the primary inlet.

7. The flow control device of claim 1, wherein the base comprises a semi-circular plate.

8. The flow control device of claim 1, wherein the base comprises:
a substantially circular plate spanning an area below both the primary and secondary inlets; and
an aperture positioned at a location corresponding to an opening at a distal end of the secondary inlet to prevent the base from occluding fluid flow from the secondary inlet into the chamber.

9. The flow control device of claim 1, further comprising a sealing member coupled to at least a portion of the base, the sealing member configured to contact an internal surface of the upper housing when the fluid level in the chamber is above the predetermined level.

10. The flow control device of claim 1, wherein the secondary inlet is disposed at a lower axial position than the primary inlet and valve member mounted therein.

11. The flow control device of claim 1, further comprising an air vent positioned on the upper housing for removing air during priming.

12. An intravenous (IV) set, comprising:
a primary IV line and a secondary IV line; and
a flow control device comprising:
an upper housing, a lower housing coupled to the upper housing, and a chamber defined between the upper and lower housings, the upper housing comprising a primary inlet fluidly communicating the primary IV line with the chamber, and a secondary inlet fluidly communicating the secondary IV line with the chamber; and
a valve member having a base disposed in the chamber and a plurality of legs extending longitudinally from the base into the primary inlet, the valve member being displaceable in a proximal direction by a buoyant force exerted on the base when a level of fluid in the chamber exceeds a predetermined level.

13. The IV set of claim 12, wherein:
the valve member blocks fluid flow through the primary inlet when the buoyant force exceeds force of fluid entering the primary inlet from the primary IV line; and
the valve member permits fluid flow through the primary inlet when a fluid level in the chamber is below predetermined level.

14. The IV set of claim 12, wherein the plurality of legs are radially spaced apart about a central longitudinal axis of the valve member, and each spacing between adjacent legs defines a flow portion through which fluid entering the primary inlet flows into the chamber.

15. The IV set of claim 14, wherein:
each of the legs comprises a portion of a flange;
the primary inlet comprises an internal surface having a circumferential lip at a distal end thereof, the circumferential lip projecting radially inwards towards a central longitudinal axis of the primary inlet; and
each flange portion is configured to be seated on the circumferential lip when the valve member is subjected to a net upstream force.

16. The IV set of claim 12, further comprising a sealing member coupled to an upper surface of the base, the sealing member configured to contact an internal surface of the upper housing when subjected to the buoyant force from fluid in the chamber.

17. The IV set of claim 12, wherein the base comprises:
a substantially circular plate sharing a common central axis with the upper housing: and
an aperture positioned at a location corresponding to an opening at a distal end of the secondary inlet to allow fluid flow from the secondary inlet into the chamber.

18. The IV set of claim 12, wherein the secondary inlet is disposed at a lower axial position than the primary inlet and valve member mounted therein.

19. A flow control device, comprising:
an upper housing, a lower housing coupled to the upper housing, and a chamber defined between the upper and lower housings, the upper housing comprising a primary inlet fluidly coupled with the chamber, and a secondary inlet fluidly coupled with the chamber; and
a valve member having a base disposed in the chamber and a plurality of legs extending longitudinally from the base into the primary inlet, the valve member being displaceable in a proximal direction by a buoyant force exerted on the base when a level of fluid in the chamber exceeds a predetermined level.

20. The flow control device of claim 19, wherein each leg of the plurality of legs is spaced apart from an adjacent leg of the plurality of legs to form a flow portion therebetween.

* * * * *